US012611195B2

(12) United States Patent　　(10) Patent No.:　US 12,611,195 B2
Maruyama　　(45) Date of Patent:　Apr. 28, 2026

(54) ULTRASOUND DIAGNOSTIC APPARATUS

(71) Applicant: FUJIFILM Healthcare Corporation, Chiba (JP)

(72) Inventor: Misaki Maruyama, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 171 days.

(21) Appl. No.: 18/536,149

(22) Filed: Dec. 11, 2023

(65) Prior Publication Data

US 2024/0188938 A1　　Jun. 13, 2024

(30) Foreign Application Priority Data

Dec. 13, 2022　(JP) ................................. 2022-198832

(51) Int. Cl.
　　*A61B 8/00*　　(2006.01)
　　*G01S 7/52*　　(2006.01)
(52) U.S. Cl.
　　CPC ........ *A61B 8/5269* (2013.01); *G01S 7/52077* (2013.01)
(58) Field of Classification Search
　　CPC ........................... G01S 7/52077; A61B 8/5269
　　See application file for complete search history.

(56) References Cited

U.S. PATENT DOCUMENTS

| 2006/0064015 A1* | 3/2006 | Davies ................ G01S 7/52028 |
| | | 600/447 |
| 2015/0094592 A1* | 4/2015 | Ravindran ............. A61B 8/488 |
| | | 600/453 |
| 2021/0161511 A1 | 6/2021 | Yoshiara et al. |
| 2021/0312594 A1 | 10/2021 | Yamanaka et al. |

FOREIGN PATENT DOCUMENTS

| JP | H07250833 | 10/1995 |
| JP | 2021083956 | 6/2021 |
| JP | 2021159511 | 10/2021 |

* cited by examiner

*Primary Examiner* — John D Li
(74) *Attorney, Agent, or Firm* — JCIPRNET

(57) ABSTRACT

A transmission/reception unit generates a plurality of reception beam data having different addition numbers of a plurality of reception channel signals which are from each oscillation element that receives reflected waves from a subject and of which phases are adjusted. An S/N estimation unit executes frequency analysis with respect to each of the plurality of reception beam data before detection processing having different addition numbers of the reception channel signals for each region. The S/N estimation unit calculates a slope of an approximate straight line of spectral intensity for the addition number of each reception channel signal for each combination of the region and a frequency domain. The slope is an S/N indicator. A signal processing unit generates a bandpass filter for each region based on the S/N indicator for each region and for each frequency domain, to apply the bandpass filter to the reception beam data before the detection processing.

4 Claims, 9 Drawing Sheets

SPECTRAL INTENSITY

AP

ADDITION NUMBER

FIG. 1

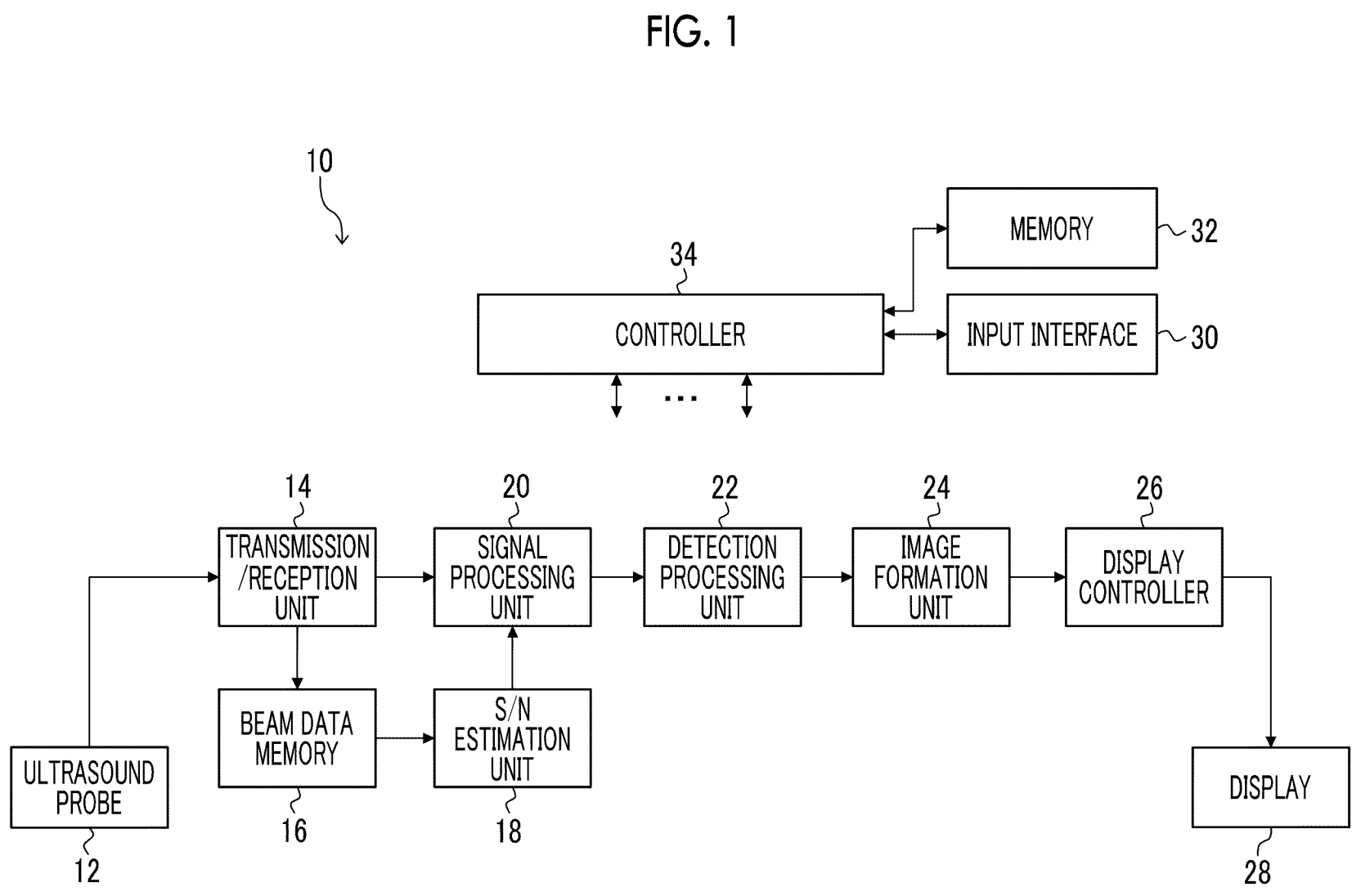

MEMORY ~32

INPUT INTERFACE ~30

CONTROLLER ~34

DISPLAY CONTROLLER ~26

DISPLAY ~28

IMAGE FORMATION UNIT ~24

DETECTION PROCESSING UNIT ~22

SIGNAL PROCESSING UNIT ~20

S/N ESTIMATION UNIT ~18

TRANSMISSION /RECEPTION UNIT ~14

BEAM DATA MEMORY ~16

ULTRASOUND PROBE ~12

Figure 11:
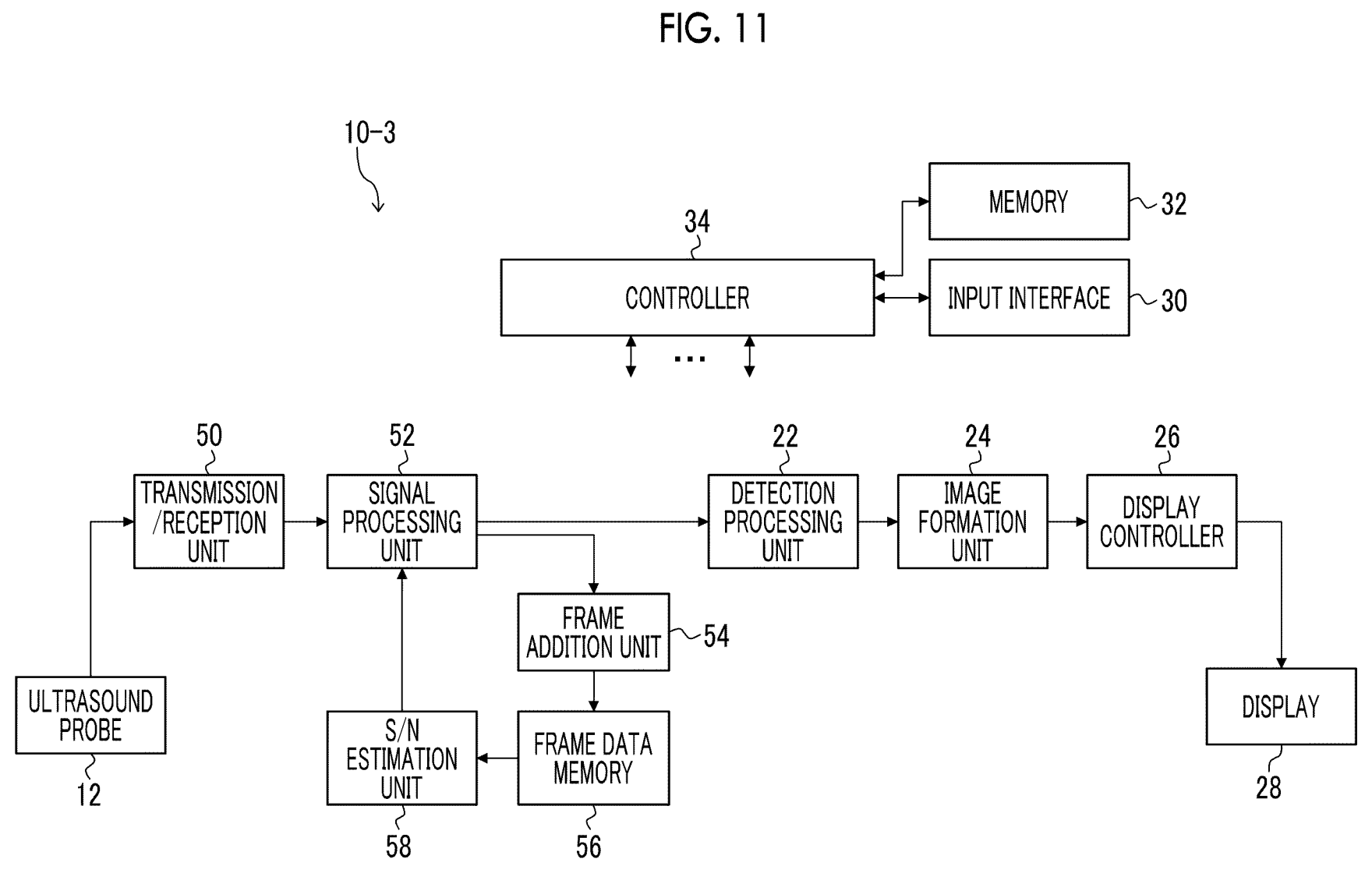

MEMORY ~32

INPUT INTERFACE ~30

CONTROLLER ~34

DISPLAY CONTROLLER ~26

DISPLAY ~28

IMAGE FORMATION UNIT ~24

DETECTION PROCESSING UNIT ~22

FRAME ADDITION UNIT ~54

FRAME DATA MEMORY ~56

SIGNAL PROCESSING UNIT ~52

S/N ESTIMATION UNIT ~58

TRANSMISSION /RECEPTION UNIT ~50

ULTRASOUND PROBE ~12

ULTRASOUND DIAGNOSTIC APPARATUS

CROSS-REFERENCE TO RELATED APPLICATION

This application claims the priority benefits of Japanese application no. 2022-198832, filed on Dec. 13, 2022. The entirety of the above-mentioned patent application is hereby incorporated by reference herein and made a part of this specification.

BACKGROUND

1. Technical Field

The present disclosure discloses an improvement of an ultrasound diagnostic apparatus.

2. Description of the Related Art

In the related art, an ultrasound diagnostic apparatus has been known, which transmits and receives ultrasound waves to and from a subject, forms reception beam data based on a reception signal obtained by transmitting and receiving the ultrasound waves, forms an ultrasound image from the reception beam data, and displays the formed ultrasound image on a display. In the ultrasound diagnostic apparatus, processing of applying a bandpass filter to the reception signal is performed for the purpose of reducing noise or the like.

In the related art, different bandpass filters have been applied for each depth of the subject.

For example, JP1995-250833A (JP-H07-250833) discloses an ultrasound diagnostic apparatus comprising a plurality of STC controllers that adjust a gain of time gain control for each depth and setting a bandpass filter applied to each depth according to the gain designated by each STC controller. Further, JP2021-83956A discloses an ultrasound diagnostic apparatus that acquires a frequency characteristic for each depth by performing frequency analysis for each depth with respect to a reception signal acquired from an ultrasound probe, and sets a bandpass filter for each depth based on the acquired frequency characteristic for each depth. Further, JP2021-159511A discloses an ultrasound diagnostic apparatus that acquires a signal characteristic value (for example, frequency) related to each depth by analyzing a reception signal acquired from an ultrasound probe, and sets a bandpass filter for each depth based on the acquired frequency for each depth.

SUMMARY

By the way, in a data space of reception beam data, in some cases, it is useful to estimate an S/N ratio for each region and for each frequency domain (of the reception beam data). It is possible to execute adaptive image quality enhancement processing of the ultrasound image for each region and for each frequency domain based on the estimated S/N ratio for each region and for each frequency domain. Examples of the adaptive image quality enhancement processing include applying a different bandpass filter for each region.

An object of an ultrasound diagnostic apparatus disclosed in the present disclosure is to provide an ultrasound diagnostic apparatus that can estimate an S/N indicator for each region and for each frequency domain in a data space of reception beam data, and enhance an image quality of an ultrasound image based on the estimated S/N indicator.

An aspect of the present disclosure relates to an ultrasound diagnostic apparatus comprising: an addition data generation unit that generates reception beam data by adding a plurality of reception channel signals, which are obtained by transmitting and receiving ultrasound waves to and from a subject and correspond to a plurality of reception channels and of which phases are adjusted by phase adjustment processing, the addition data generation unit generating a plurality of the reception beam data having different addition numbers of the reception channel signals; an S/N estimation unit that executes frequency analysis with respect to each of the plurality of reception beam data before detection processing having different addition numbers of the reception channel signals for each predetermined region in a data space of the reception beam data, to estimate an S/N indicator based on an increase amount of spectral intensity accompanying an increase of the addition number for each region and for each frequency domain; and an image quality enhancement unit that executes different types of image quality enhancement processing for each region to enhance an image quality of an ultrasound image based on the S/N indicator estimated for each region and for each frequency domain.

Signal components of the plurality of reception channel signals which are obtained by the same transmission beam and subjected to the phase adjustment processing corresponding to the plurality of reception channels are signals having substantially the same phase and substantially the same amplitude. Therefore, ideally, in a case in which N reception channel signals are added, each signal component in each frequency domain is multiplied by about N. On the other hand, the phases and the amplitudes of noise components of the respective reception channel signals vary. Therefore, even in a case in which N noise components are added, the noise component in each frequency domain is not multiplied by N and is only a value smaller than the value multiplied by N. In general, an effective value in a case in which a plurality of pieces of uncorrelated noise are added is represented by the square root of the sum of squares of the effective values of the respective noises, and in a case in which N noise components of each reception channel are added, the noise component in each frequency domain is approximately multiplied by v N.

Therefore, as the number of the signal components of the reception beam data in a certain region is increased, the S/N indicator is increased as the addition number is increased. In other words, an increase amount of the spectral intensity for the addition number of the reception channel signals represents the S/N indicator. The S/N estimation unit can estimate the S/N indicator for each region and for each frequency domain by calculating the increase amount of the spectral intensity for the addition number of the reception channel signals for each region and for each frequency domain. As a result, the image quality enhancement unit can perform the image quality enhancement processing of the ultrasound image based on the S/N indicator for each region and for each frequency domain.

An aspect of the present disclosure relates to an ultrasound diagnostic apparatus comprising: a reception beam data generation unit that generates reception beam data by phase adjustment addition processing with respect to a plurality of reception channel signals, which are obtained by transmitting and receiving ultrasound waves to and from a subject and correspond to a plurality of reception channels; an addition data generation unit that generates addition reception beam data by adding a plurality of the reception beam data corresponding to the same scanning line position, the addition data generation unit generating a plurality of the addition reception beam data having different addition numbers of the plurality of reception beam data; an S/N estimation unit that executes frequency analysis with respect to each of the plurality of addition reception beam data before detection processing for each predetermined region in a data space of the reception beam data, to estimate an S/N indicator based on an increase amount of spectral intensity accompanying an increase of the addition number for each region and for each frequency domain; and an image quality enhancement unit that executes different types of image quality enhancement processing for each region to enhance an image quality of an ultrasound image based on the S/N indicator estimated for each region and for each frequency domain.

In this configuration as well, as the number of the signal components of the reception beam data in a certain region is increased, the S/N indicator is increased as the addition number of the reception beam data corresponding to the same scanning line position is increased. In other words, the increase amount of the spectral intensity for the addition number of the reception beam data represents the S/N indicator. The S/N estimation unit can estimate the S/N indicator for each region and for each frequency domain by calculating the increase amount of the spectral intensity for the addition number of the reception beam data for each region and for each frequency domain. As a result, the image quality enhancement unit can perform the image quality enhancement processing of the ultrasound image based on the S/N indicator for each region and for each frequency domain.

The image quality enhancement unit may generate a bandpass filter for each region based on the S/N indicator estimated for each region and for each frequency domain, to apply the generated bandpass filter for each region to the reception beam data before the detection processing.

With this configuration, a different bandpass filter for each region can be applied, and the noise can be appropriately reduced for each region.

The addition data generation unit may generate the addition reception beam data by inter-transmission aperture synthesis, to generate the plurality of addition reception beam data having different addition numbers of the reception beam data in the inter-transmission aperture synthesis.

The addition data generation unit may generate the addition reception beam data by adding frame data, which are the plurality of reception beam data for one frame, to generate the plurality of addition reception beam data having different addition numbers of the frame data.

The S/N estimation unit may calculate a slope of an approximate straight line of the spectral intensity for each addition number in a two-dimensional data space of the addition number and the spectral intensity for each region and for each frequency domain, to estimate the calculated slope as the S/N indicator for each region and for each frequency domain.

With this configuration, the S/N indicator for each region and for each frequency domain can be estimated by obtaining the slope of the approximate straight line of the spectral intensity for the addition number of the reception channel signals or the reception beam data.

The S/N estimation unit may calculate corrected spectral intensity obtained by correcting the spectral intensity based on a predetermined correction coefficient for each addition number, to estimate the slope of the approximate straight line of the corrected spectral intensity for each addition number in the two-dimensional data space as the S/N indicator.

With this configuration, in a case in which the reception channel signals, which are addition targets, are not the same signal or in a case in which the reception beam data, which are addition targets, are not the same signal, it is possible to estimate the S/N indicator while reducing the influence of a difference in the spectral intensity between the reception channels or between the reception beam data.

With the ultrasound diagnostic apparatus disclosed in the present disclosure, it is possible to enhance the image quality of the ultrasound image based on the S/N indicator for each region and for each frequency domain in the data space of the reception beam data.

BRIEF DESCRIPTION OF THE DRAWINGS

FIG. 1 is a schematic configuration diagram of an ultrasound diagnostic apparatus according to a first embodiment.

FIG. 11 is a schematic configuration diagram of an ultrasound diagnostic apparatus according to a third embodiment.

DESCRIPTION OF THE EMBODIMENTS

First Embodiment

Figure 2A:
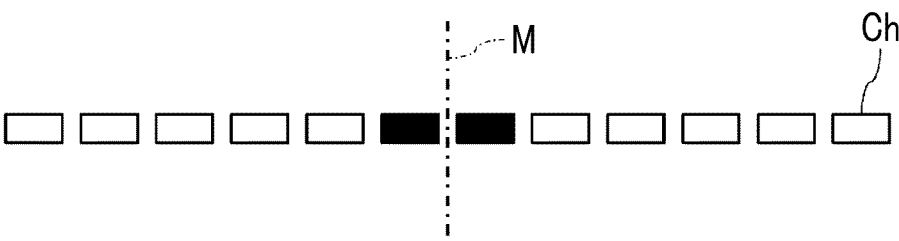
FIG. 2A is a first diagram showing a reception channel that is an addition target.
Figure 2B:
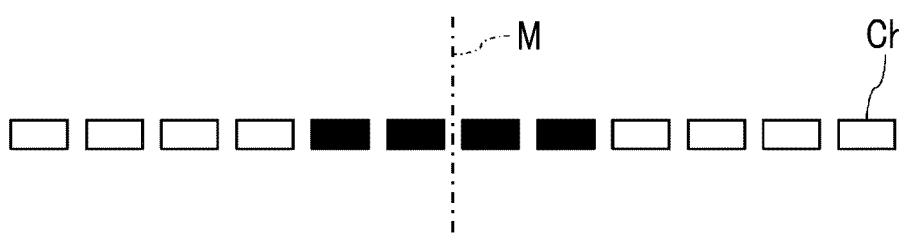
FIG. 2B is a second diagram showing the reception channel that is the addition target.
Figure 2C:
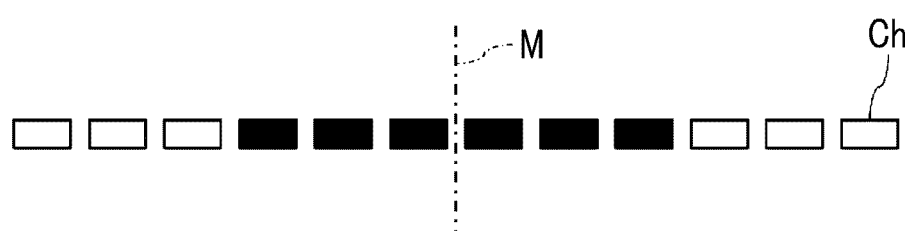
FIG. 2C is a third diagram showing the reception channel that is the addition target.
Figure 2D:
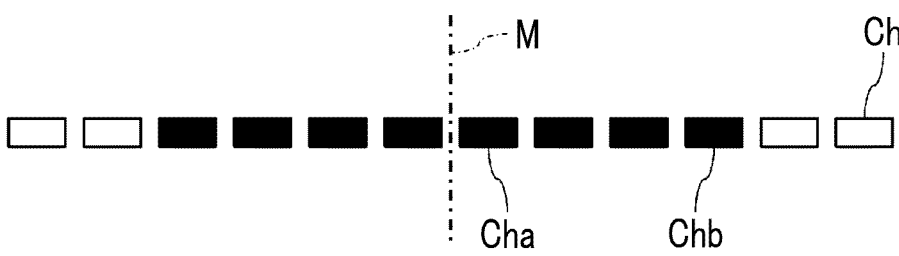
FIG. 2D is a fourth diagram showing the reception channel that is the addition target.

FIG. 1 is a schematic configuration diagram of an ultrasound diagnostic apparatus 10 according to a first embodiment. The ultrasound diagnostic apparatus 10 is a medical apparatus that is installed in a medical institution, such as a hospital, and is used during an ultrasound examination.

The ultrasound diagnostic apparatus 10 is an apparatus that scans a subject with an ultrasound beam to form an ultrasound image based on a reception signal obtained by the scanning. For example, the ultrasound diagnostic apparatus 10 forms a tomographic image (B-mode image) in which the amplitude intensity of reflected waves from a scanning surface is transformed into the brightness based on the reception signal. Alternatively, the ultrasound diagnostic apparatus 10 can also form a Doppler image, which is an ultrasound image showing a motion velocity of a tissue in the subject, based on a difference (Doppler shift) between frequencies of transmitted waves and received waves. In the present embodiment, processing of forming the B-mode image by the ultrasound diagnostic apparatus 10 will be described.

An ultrasound probe 12 is a device that transmits and receives ultrasound waves to and from the subject. The ultrasound probe 12 has an oscillation element array including a plurality of oscillation elements that transmit and receive the ultrasound waves to and from the subject.

A transmission/reception unit 14 transmits a transmission signal to the ultrasound probe 12 (specifically, each oscillation element of the oscillation element array) under the control of a controller 34 (described later). As a result, the ultrasound waves are transmitted from each oscillation element toward the subject. The ultrasound waves are transmitted from the plurality of oscillation elements at a time, and ultrasound beams (transmission beams) are transmitted to the transmission/reception unit 14 in a plurality of directions from the plurality of oscillation elements by controlling a transmission timing of the ultrasound waves from each oscillation element. In addition, the transmission/reception unit 14 receives a reception signal from each oscillation element that receives the reflected waves from the subject. In the present disclosure, the reception signal received from each oscillation element is referred to as a reception signal of each reception channel, and the reception signal of the reception channel is referred to as a reception channel signal.

The transmission/reception unit 14 includes a plurality of delayers corresponding to the respective reception channels, and the plurality of delayers perform phase adjustment processing of aligning phases of a plurality of reception channel signals.

In addition, the transmission/reception unit 14 includes an adder, and the adder adds the plurality of reception channel signals obtained by the same transmission beam and subjected to the phase adjustment processing to generate reception beam data. One reception beam data is data corresponding to one scanning line of the ultrasound waves (scan line; in other words, a transmission direction of the transmission beam), and is data including information indicating the signal intensity of the reflected waves from each depth of the subject.

The transmission/reception unit 14 generates a plurality of reception beam data having different addition numbers of the plurality of reception channel signals of which the phases are adjusted, by the control from the controller 34. FIGS. 2A to 2D and 3A to 3D are diagrams showing a reception channel Ch that is an addition target. In FIGS. 2A to 2D and 3A to 3D, 12 reception channels Ch included in an effective reception aperture are shown as a simulated example. A one-point chain line indicates a center M of the effective reception aperture. The center M of the effective reception aperture is also the transmission direction (center)

of the transmission beam. In FIGS. 2A to 2D and 3A to 3D, the reception channel Ch shown in black indicates the reception channel Ch in which the reception channel signal is the addition target, and the reception channel Ch shown in white indicates the reception channel Ch in which the reception channel signal is not the addition target.

As shown in FIGS. 2A to 2D, for example, the transmission/reception unit 14 generates the plurality of reception beam data of reception beam data (FIG. 2A) to which the reception channel signals of two reception channels Ch are added, reception beam data (FIG. 2B) to which the reception channel signals of four reception channels Ch are added, reception beam data (FIG. 2C) to which the reception channel signals of six reception channels Ch are added, and reception beam data (FIG. 2D) to which the reception channel signals of eight reception channels Ch are added. It should be noted that all the reception channel signals of each reception channel Ch are stored in a reception channel memory (not shown) regardless of whether or not the reception channel signals are added for generating the reception beam data. Therefore, the transmission/reception unit 14 need only select the reception channel to be used for generating the reception beam data (that is, used as the addition target) from the plurality of reception channel signals stored in the reception channel memory.

Figure 3A:
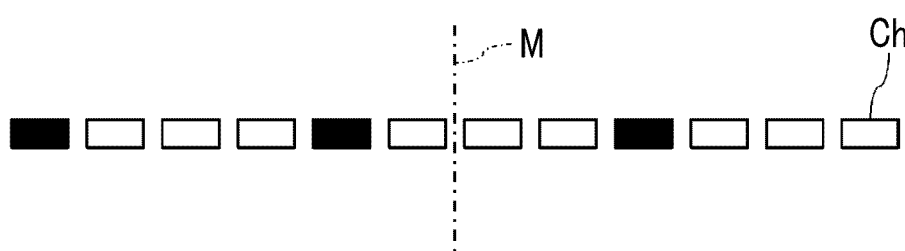
FIG. 3A is a fifth diagram showing the reception channel that is the addition target.
Figure 3B:
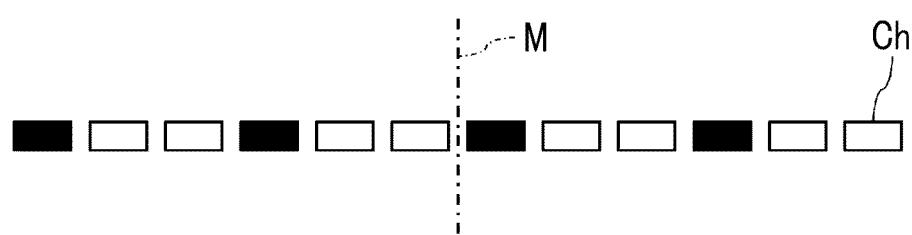
FIG. 3B is a sixth diagram showing the reception channel that is the addition target.
Figure 3C:
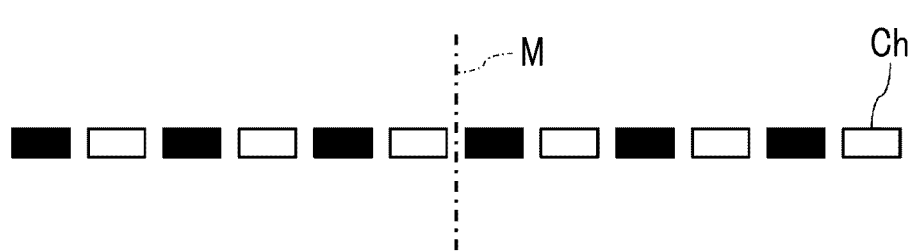
FIG. 3C is a seventh diagram showing the reception channel that is the addition target.
Figure 3D:
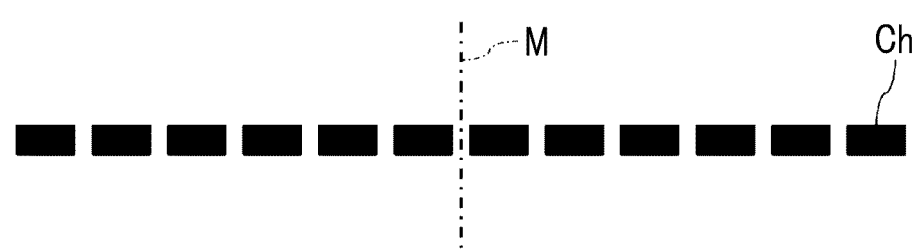
FIG. 3D is an eighth diagram showing the reception channel that is the addition target.

In FIGS. 2A to 2D, the reception channel signal of the reception channel Ch on the center M side of the effective reception aperture is added, but such a case does not always have to be adopted. For example, as shown in FIGS. 3A to 3C, the reception channel Ch to which the reception channel signals are added may be selected at one or a plurality of intervals from the end of the effective reception aperture. In the example shown in FIGS. 3A to 3D, the transmission/reception unit 14 generates the plurality of reception beam data of reception beam data (FIG. 3A) to which the reception channel signals of three reception channels Ch are added, reception beam data (FIG. 3B) to which the reception channel signals of four reception channels Ch are added, reception beam data (FIG. 3C) to which the reception channel signals of six reception channels Ch are added, and reception beam data (FIG. 3D) to which the reception channel signals of 12 reception channels Ch are added.

In the present embodiment, the transmission/reception unit 14 generates the plurality of reception beam data for one frame having different addition numbers of the reception channel signals. In the present disclosure, the reception beam data for one frame is referred to as frame data. The frame data corresponds to one ultrasound image. It should be noted that the transmission/reception unit 14 does not always have to generate the reception beam data for the entire one frame for one addition number, and need only generate the reception beam data that covers at least a target region for enhancing an image quality of the ultrasound image.

In the first embodiment, as described above, the transmission/reception unit 14 corresponds to an addition data generation unit.

Figure 4:
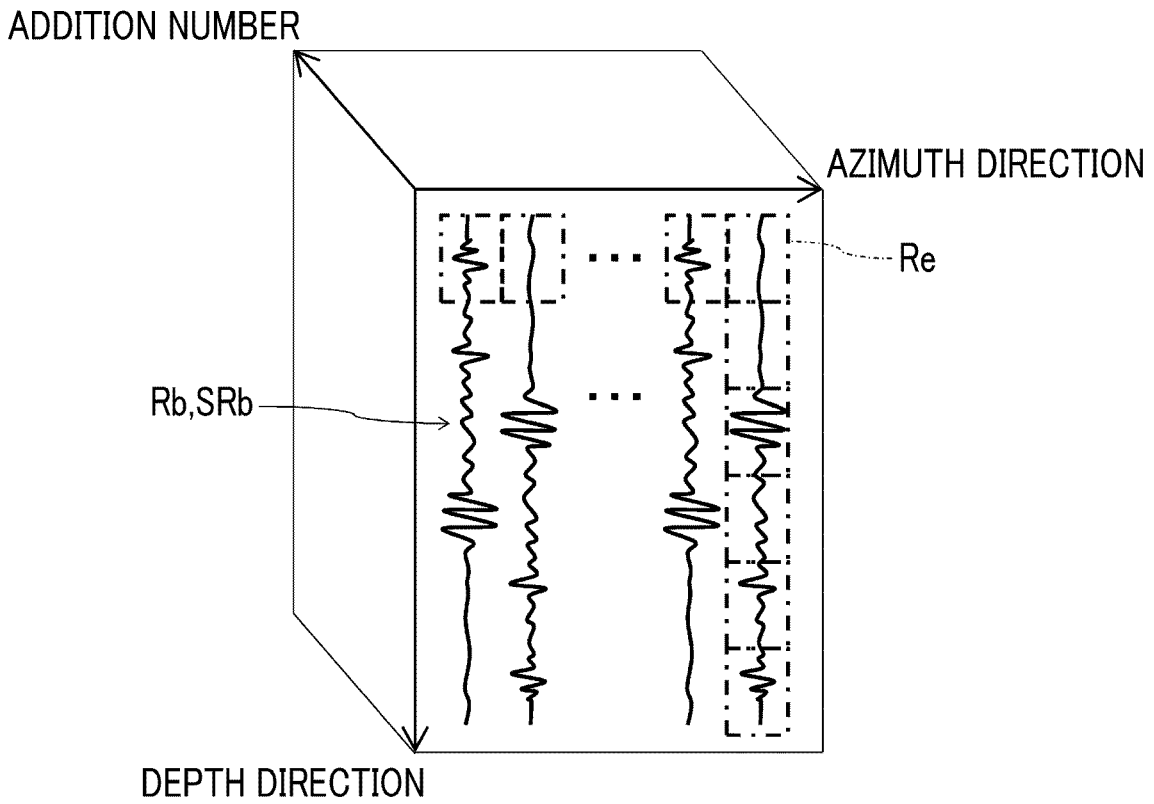
FIG. 4 is a conceptual diagram showing a plurality of reception beam data which have different addition numbers of reception channel signals and are stored in a beam data memory.

A plurality of reception beam data having different addition numbers of the reception channel signals generated by the transmission/reception unit 14 are stored in a beam data memory 16. FIG. 4 is a conceptual diagram showing a plurality of reception beam data Rb which have different addition numbers of the reception channel signals and are stored in the beam data memory 16. In FIG. 4, one frame of reception beam data Rb (that is, the frame data) corresponding to one addition number is represented in a two-dimensional data space in the azimuth direction and the depth direction. Further, in FIG. 4, a plurality of frame data having different addition numbers are arranged in an addition number direction orthogonal to the azimuth direction and the depth direction.

A plurality of regions Re are defined in advance in a data space of the reception beam data Rb. In the present embodiment, the plurality of regions Re arranged in a two-dimensional direction without gaps in the data space of the reception beam data Rb for one frame are defined. It should be noted that the region Re does not always have to cover the entire data space of the reception beam data Rb for one frame, and need only be defined to cover at least the target region for enhancing the image quality of the ultrasound image. Each region Re of the reception beam data Rb in the data space corresponds to each region on the ultrasound image. In the present disclosure, the region on the ultrasound image corresponding to the region Re in the data space of the reception beam data Rb is also referred to as the region Re for the sake of convenience.

Figure 5:
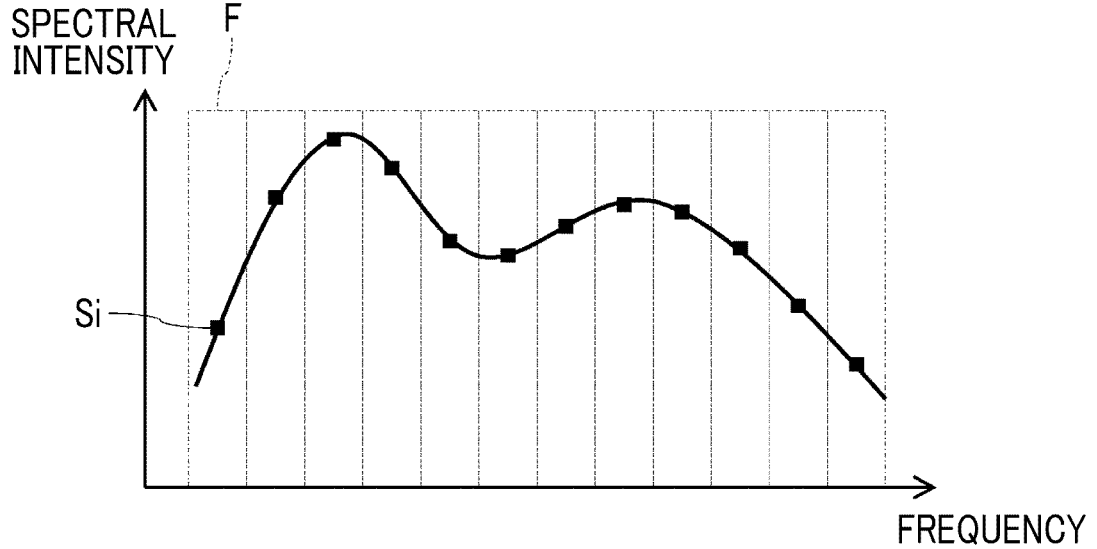
FIG. 5 is a diagram showing a frequency spectrum of the reception beam data corresponding to one addition number in one region.

The S/N estimation unit 18 executes frequency analysis (for example, fast Fourier transform (FFT)) with respect to each of the plurality of reception beam data Rb before the detection processing (that is, having frequency information) having different addition numbers of the reception channel signals for each region Re. FIG. 5 is a diagram showing a frequency spectrum of the reception beam data Rb corresponding to one addition number in one region Re. By the frequency analysis processing by the S/N estimation unit 18, the frequency spectrum is acquired for each region Re and for each addition number of the reception channel signals.

As shown in FIG. 5, a plurality of frequency domains F are defined in advance. The frequency domain F indicates a certain frequency range (for example, Hz to xx Hz). Then, the S/N estimation unit 18 calculates spectral intensity Si for each frequency domain F based on the acquired frequency spectrum. The spectral intensity Si may be a representative value (for example, an average value or a median value) of the spectral intensity included in the frequency domain F. As a result, the spectral intensity Si is acquired for each region Re, for each addition number of the reception channel signals, and for each frequency domain F.

Figure 6:
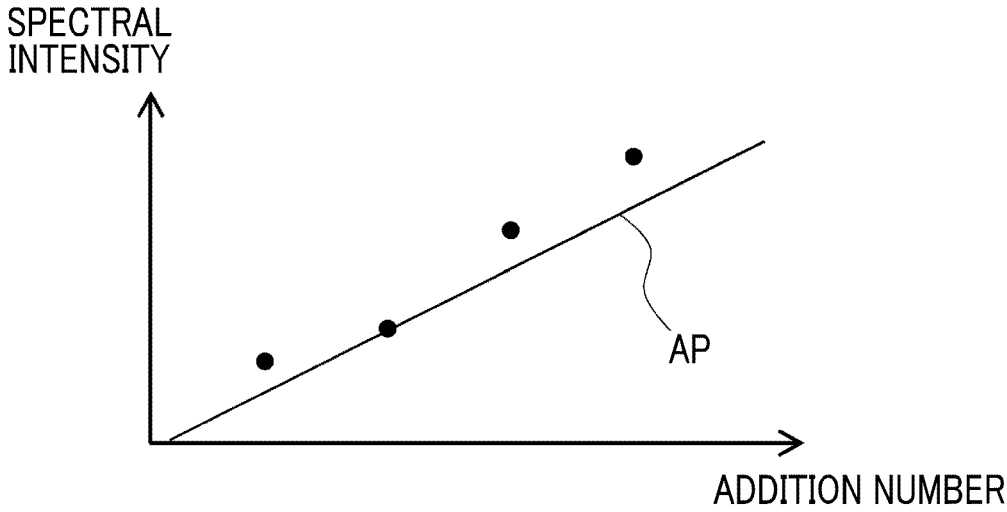
FIG. 6 is a diagram showing a relationship between the addition number of the reception channel signals and spectral intensity in one region and one frequency domain.

FIG. 6 is a diagram showing a relationship between the addition number and the spectral intensity in one region Re and one frequency domain F. The S/N estimation unit 18 plots the spectral intensity for the addition number of each reception channel signals for one region Re and one frequency domain F in the two-dimensional data space of the addition number of the reception channel signals and the spectral intensity. Then, the S/N estimation unit 18 obtains an approximate straight line AP of the plotted spectral intensity for the addition number of each of the reception channel signals, and calculates a slope of the approximate straight line AP.

Here, the slope of the approximate straight line AP is a parameter indicating an S/N indicator of the region Re in the frequency domain F. The S/N indicator indicates a ratio of the signal component to the noise component, a larger S/N indicator indicates that the number of the noise components is smaller and the number of the signal components is larger, and a smaller S/N indicator indicates that the number of the noise components is larger and the number of the signal components is smaller.

With reference to FIGS. 2A to 2D or 3A to 3D, the signal components of the reception channel signals, which are subjected to the phase adjustment processing, of the respective reception channels Ch included in the effective reception aperture for the same transmission beam are signals having substantially the same phase and substantially the same amplitude. Therefore, ideally, in a case in which N signal components are added, the signal components in each frequency domain F are each multiplied by about N. On the other hand, the phases and the amplitudes of noise components of the respective reception channel signals vary. Therefore, even in a case in which N noise components are added, the noise component in each frequency domain F is not multiplied by N and is only a value smaller than the value multiplied by N. In a case in which N noise components of each reception channel Ch are added, the noise components of each frequency domain F are approximately multiplied by $\sqrt{N}$.

Therefore, as the number of the signal components of the reception beam data Rb in a certain region Re is increased, the S/N indicator is increased as the addition number is increased. In other words, the slope of the approximate straight line AP of the spectral intensity for the addition number of each reception channel signal represents the S/N indicator. For example, ideally, in a case in which all the reception beam data Rb are the signal components, in a case in which the addition number is N, the spectral intensity is also multiplied by N, so that the slope of the approximate straight line AP is N/N, that is, 1. On the contrary, in a case in which all the reception beam data Rb are the noise components, the spectral intensity is multiplied by $\sqrt{N}$ in a case in which the addition number is N, so that the slope of the approximate straight line AP is only multiplied by $\sqrt{N}/N$. As the signal component of the reception beam data Rb is increased (noise component is decreased), the slope of the approximate straight line AP is increased from $\sqrt{N}/N$ to 1.

As described above, ideally, the signal components of the signals, which are subjected to the phase adjustment processing, of the respective reception channels Ch included in the effective reception aperture for the same transmission beam are substantially the same signal. However, there may be a case in which the signal components of the signals, which are subjected to the phase adjustment processing, of the respective reception channels Ch do not be the same signal. For example, in general, since the oscillation element of the ultrasound probe 12 has sensitivity directivity depending on the element size and the frequency of the signal, the signal component of the reception channel Ch (for example, a reception channel Cha in FIG. 2D) close to the center of the transmission beam is larger than the signal component of the reception channel Ch (for example, a reception channel Chb in FIG. 2D) far from the center of the transmission beam. In this case, ideally, even in a case in which all the reception beam data Rb are the signal components, the spectral intensity may not be multiplied by N in a case in which the addition number is N.

Figure 7:
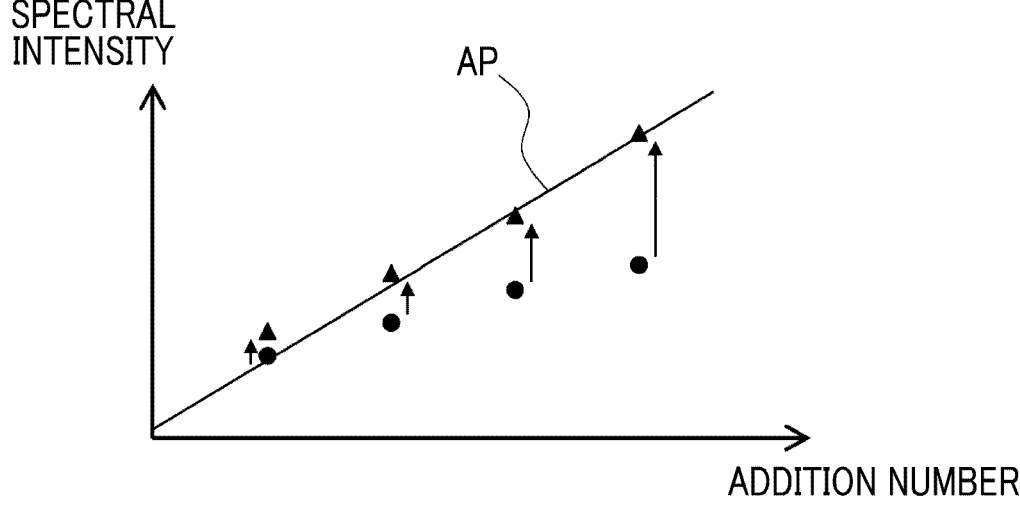
FIG. 7 is a diagram showing spectral intensity corrected by a correction coefficient.

Therefore, the S/N estimation unit 18 may correct the spectral intensity for each addition number based on a correction coefficient defined in advance for each addition number of the reception channel signals. The correction coefficient need only be defined in advance based on the position of the reception channel Ch, which is the addition target, with respect to the center of the transmission beam in each addition number of the reception channel signals, and need only be stored in the memory 32. Then, as shown in FIG. 7, the S/N estimation unit 18 calculates corrected spectral intensity (black triangle in FIG. 7) obtained by correcting the spectral intensity (black circle in FIG. 7) for each addition number based on the correction coefficient for each addition number. Then, the S/N estimation unit 18 may obtain the approximate straight line AP of the corrected spectral intensity for each addition number in the two-dimensional data space of the addition number of the reception channel signals and the spectral intensity, to estimate the slope of the approximate straight line AP as the S/N indicator.

The S/N estimation unit 18 performs the processing described above for each combination of the region Re and the frequency domain F, and calculates the slope of the approximate straight line AP for each combination of the region Re and the frequency domain F. That is, the S/N estimation unit 18 estimates the S/N indicator for each combination of the region Re and the frequency domain F based on the increase amount of the spectral intensity accompanying the increase of the addition number of the reception channel signals.

Figure 8:
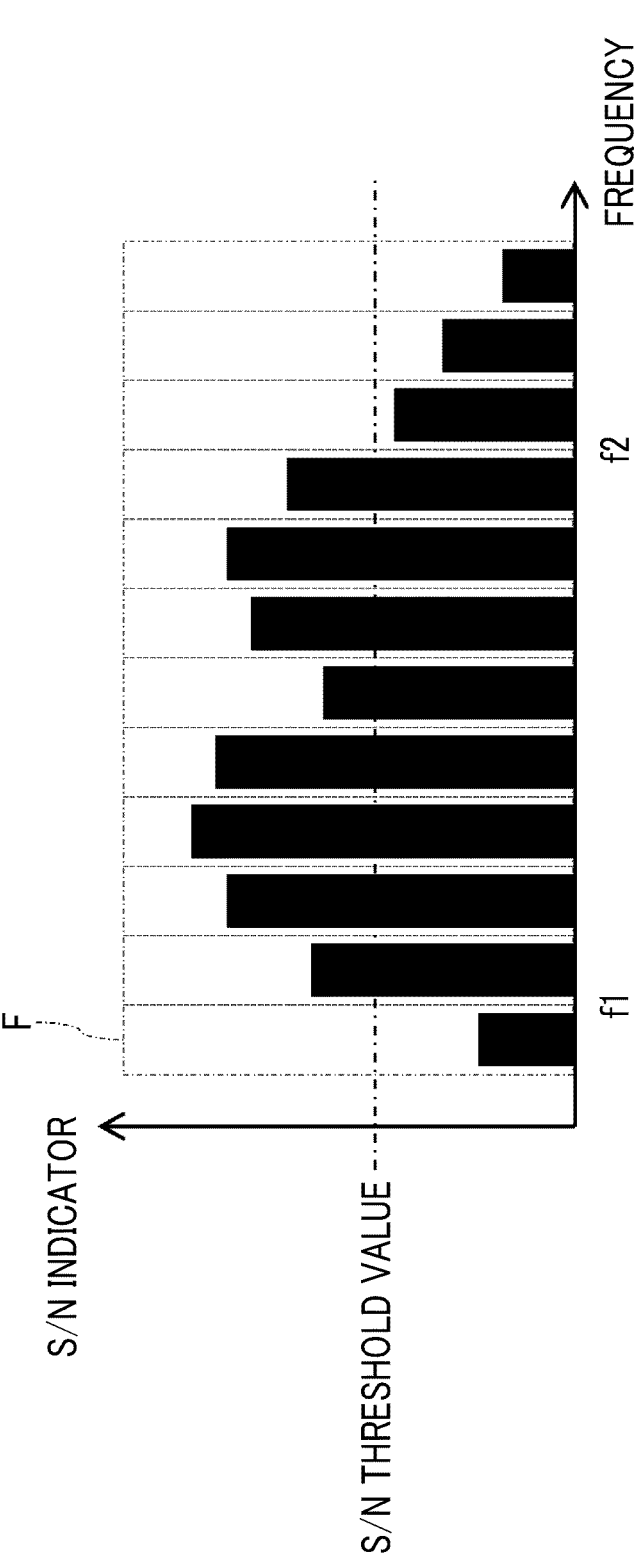
FIG. 8 is a diagram showing an S/N indicator for each frequency domain in one region.

FIG. 8 is a diagram showing the S/N indicator for each frequency domain F in one region Re. As described above, since the S/N estimation unit 18 estimates the S/N indicator for each combination of the region Re and the frequency domain F, for one region Re, as shown in FIG. 8, the S/N indicator is estimated for each frequency domain F.

The signal processing unit 20 executes various types of signal processing including, for example, filter processing of applying a bandpass filter to the reception beam data from the transmission/reception unit 14. In particular, the signal processing unit 20 generates the bandpass filter for each region Re based on the S/N indicator, for each region Re and for each frequency domain F, which is estimated by the S/N estimation unit 18.

With reference to FIG. 8, specifically, the signal processing unit 20 generates, for each region Re, the bandpass filter that passes signals in the frequency domain F in which the estimated S/N indicator is equal to or larger than a predetermined S/N threshold value. For example, for the region Re having the S/N indicator for each frequency domain F shown in FIG. 8, the bandpass filter that passes signals from a frequency f1 to a frequency f2 is generated. Since the S/N indicators for each frequency domain F may be different from each other between the respective regions Re, the bandpass filters generated for the respective regions Re may also be different from each other.

The signal processing unit 20 applies the bandpass filter generated for each region Re to the reception beam data Rb before the detection processing as the image quality enhancement processing of enhancing the image quality of the ultrasound image. In other words, even in a case in which the S/N indicator for each frequency domain F is different for each region Re, the bandpass filter suitable for each region Re can be applied. As a result, it is possible to adaptively enhance the image quality of each region Re of the ultrasound image. For example, in the ultrasound image, appropriate noise reduction can be executed without excessively performing noise suppression for each position (region Re) and impairing resolution. As described above, the signal processing unit 20 corresponds to an image quality enhancement unit.

The signal processing unit 20 can apply the bandpass filter described above to the reception beam data Rb (that is, the frame data obtained by the same transmission beam) of the same frame as the plurality of reception beam data Rb, which are stored in the beam data memory 16 and have different addition numbers of the reception channel signals.

In addition, from the viewpoint of suppressing delay due to the generation processing of the plurality of reception beam data Rb having different addition numbers of the reception channel signals, the estimation processing of the S/N indicator by the S/N estimation unit 18, and the like, the signal processing unit 20 may set the reception beam data Rb that is an application target of the bandpass filter as the reception beam data Rb of one or a plurality of frames after the plurality of reception beam data Rb having different addition numbers of the reception channel signals for generating the bandpass filter.

Further, in a case in which there is no change in the cross section of the subject shown in the ultrasound image, it is considered that the S/N indicator of each frequency domain F in each region Re is not changed so much. Therefore, the signal processing unit 20 may continue to use the bandpass filter of each region Re once generated until the cross section of the subject shown in the ultrasound image is changed. Whether or not the cross section of the subject shown in the ultrasound image is changed can be determined by comparing, between the frames, the ultrasound images formed by an image formation unit 24 described later. Alternatively, an acceleration sensor may be provided in the ultrasound probe 12 to detect a posture of the ultrasound probe 12 based on a signal from the acceleration sensor and to determine that the cross section of the subject shown in the ultrasound image is changed, depending on the change of the posture of the ultrasound probe 12.

A detection processing unit 22 executes processing, such as detection processing (for example, envelope detection processing) or logarithmic compression processing, with respect to the reception beam data Rb after the processing by the signal processing unit 20. The reception beam data Rb loses the phase information (frequency information) due to the detection processing by the detection processing unit 22.

An image formation unit 24 forms the ultrasound image (B-mode image) based on the frame data subjected to the detection processing or the like by the detection processing unit 22.

A display controller 26 performs control of displaying, on a display 28, the ultrasound image formed by the image formation unit 24 and various types of other information. The display 28 is, for example, a display device configured of a liquid crystal display, an organic electro luminescence (EL), or the like.

An input interface 30 is configured of, for example, a button, a track ball, a touch panel, or the like. The input interface 30 is used to input a command from a user to the ultrasound diagnostic apparatus 10.

A memory 32 includes a hard disk drive (HDD), a solid state drive (SSD), an embedded multi media card (eMMC), a read only memory (ROM), or the like. The memory 32 stores an ultrasound diagnostic program for operating each of the units of the ultrasound diagnostic apparatus 10. It should be noted that the ultrasound diagnostic program can also be stored, for example, in a computer-readable non-transitory storage medium, such as a universal serial bus (USB) memory or a CD-ROM. The ultrasound diagnostic apparatus 10 can read and execute the ultrasound diagnostic program from such a storage medium.

The controller 34 includes at least one of a general-purpose processor (for example, a central processing unit (CPU)) or a dedicated processor (for example, a graphics processing unit (GPU), an application specific integrated circuit (ASIC), a field-programmable gate array (FPGA), a programmable logic device, and the like). The controller 34 may be configured by the cooperation of a plurality of processing devices that are present at physically separated positions, instead of being configured of one processing device. The controller 34 controls each of the units of the ultrasound diagnostic apparatus 10 according to the ultrasound diagnostic program stored in the memory 32.

It should be noted that each of the units of the units of the transmission/reception unit 14, the S/N estimation unit 18, the signal processing unit 20, the detection processing unit 22, the image formation unit 24, and the display controller 26 is configured of one or a plurality of processors, chips, electric circuits, or the like. Each of these units may be realized by the cooperation between hardware and software.

Second Embodiment

Figure 9:
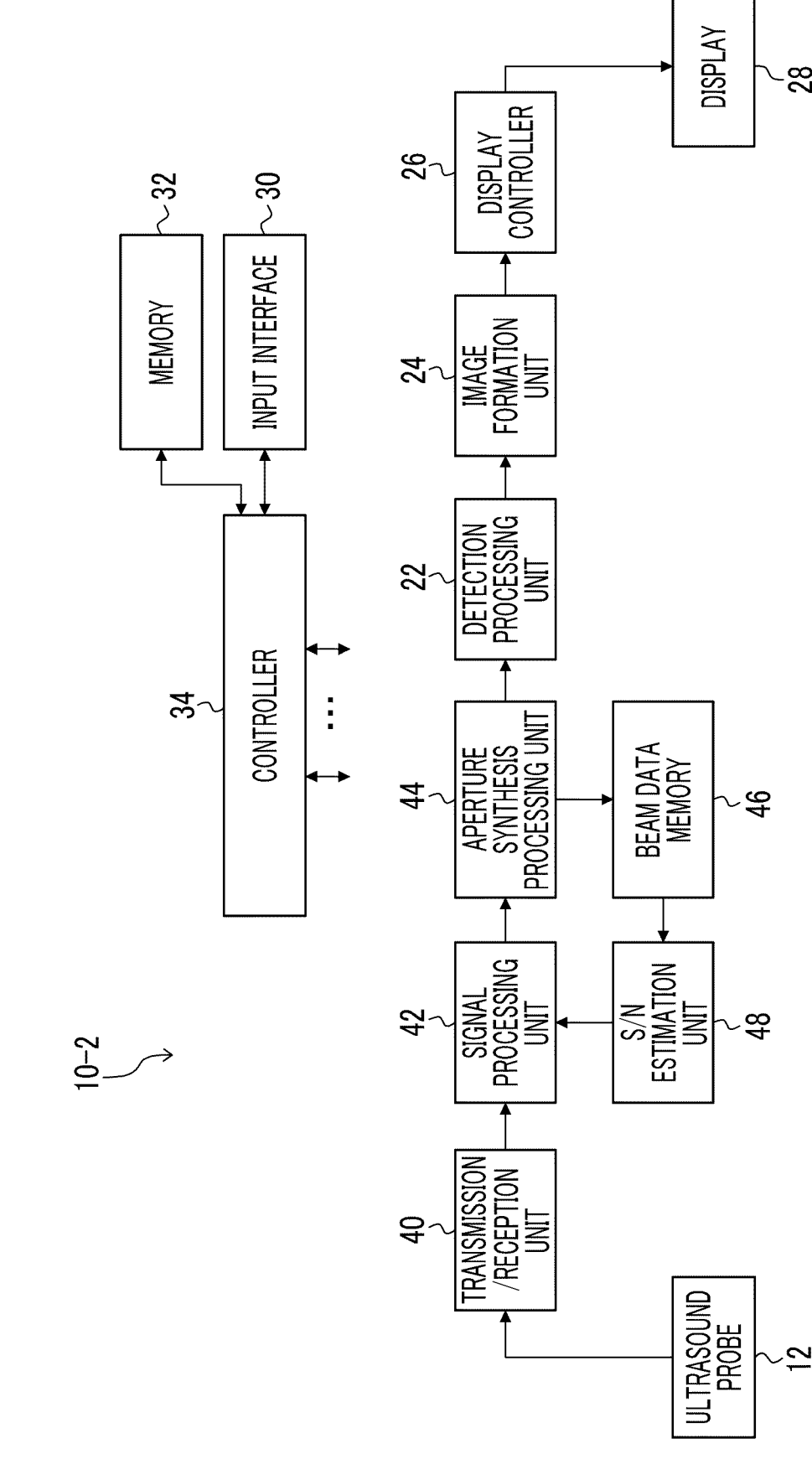
FIG. 9 is a schematic configuration diagram of an ultrasound diagnostic apparatus according to a second embodiment.

FIG. 9 is a schematic configuration diagram of an ultrasound diagnostic apparatus 10-2 according to a second embodiment. In FIG. 9, components that execute the same processing as the processing of the ultrasound diagnostic apparatus 10 according to the first embodiment are designated by the same reference numerals as the reference numerals in FIG. 1, and the description thereof will be omitted.

A transmission/reception unit 40 as a reception beam data generation unit transmits the transmission signal to the ultrasound probe 12 under the control of the controller 34. As a result, the ultrasound waves are transmitted from each oscillation element toward the subject. The ultrasound waves are transmitted from the plurality of oscillation elements at a time, and the ultrasound beams are transmitted to the transmission/reception unit 40 in the plurality of directions from the plurality of oscillation elements by controlling the transmission timing of the ultrasound waves from each oscillation element. In addition, the transmission/reception unit 40 receives a reception channel signal from each oscillation element that receives the reflected waves from the subject. The transmission/reception unit 40 executes phase adjustment addition processing with respect to the plurality of reception channel signals corresponding to a plurality of reception channels, thereby generating the reception beam data Rb.

The signal processing unit 42 executes various types of signal processing including, for example, the filter processing of applying the bandpass filter to the reception beam data Rb from the transmission/reception unit 40. In particular, the signal processing unit 42 generates the bandpass filter for each region Re based on the S/N indicator, for each region Re and for each frequency domain F, which is estimated by an S/N estimation unit 48 described later. Details of generation processing of the bandpass filter will be described later.

In addition, the signal processing unit 42 may not perform (may skip) the bandpass filter processing with respect to the reception beam data Rb used by the S/N estimation unit 48 described later. Alternatively, as the preprocessing, the bandpass filter processing having a wide band characteristic that cuts only a component in the vicinity of direct current (DC) may be performed.

The reception beam data Rb subjected to the signal processing by the signal processing unit 42 is held in a memory (not shown) called an LRI memory. The LRI memory has at least a memory capacity capable of storing the reception beam data Rb enough to generate the addition reception beam data for one frame by aperture synthesis processing described later.

Figure 10:
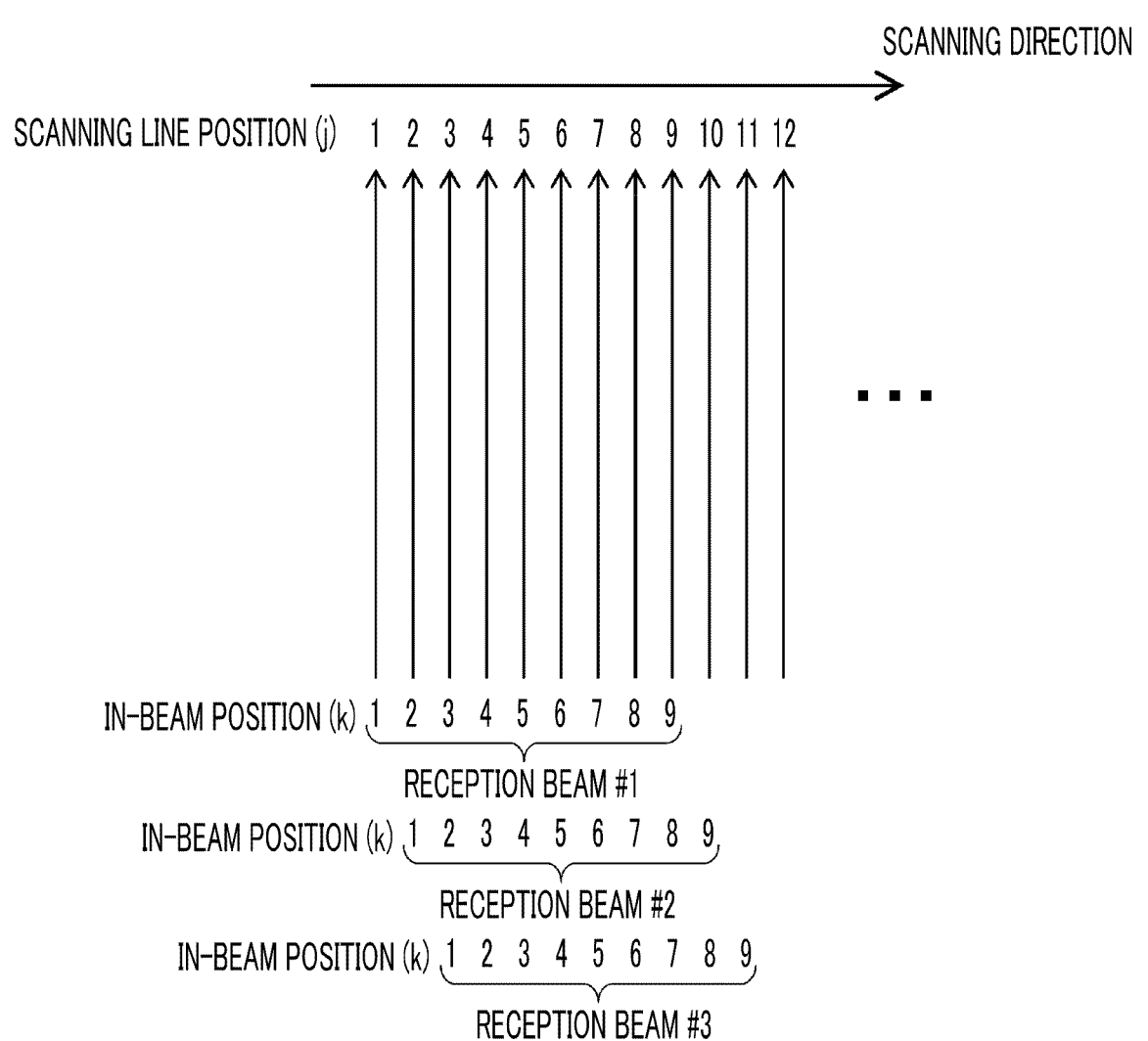
FIG. 10 is a diagram showing a scanning line position and an in-beam position in inter-transmission aperture synthesis.

An aperture synthesis processing unit 44 executes inter-transmission aperture synthesis of adding the plurality of reception beam data obtained based on different transmission beams. The inter-transmission aperture synthesis will be described with reference to FIG. 10. In FIG. 10, scanning line positions are shown in the horizontal direction, and the scanning line positions are numbered in order from the end. In the present disclosure, the scanning line position is represented by a variable j.

The transmission/reception unit 40 transmits a first transmission beam (hereinafter, referred to as "transmission beam #1"), and generates the plurality of reception beam data Rb (hereinafter, the plurality of reception beam data Rb corresponding to the transmission beam #1 is referred to as "reception beam #1") corresponding to the plurality of scanning line positions for the first transmission beam. In the example of FIG. 10, the transmission/reception unit 40 transmits the transmission beam #1 centered on the scanning line position j=5, thereby generating the reception beam #1 corresponding to the scanning line positions j=1 to 9. In the present disclosure, in the plurality of reception beam data Rb for one transmission beam, in-beam positions are numbered in order from the end. In the present disclosure, the in-beam position is represented by a variable k. In the reception beam #1, k=j. It should be noted that the example of FIG. 10 is a diagram simulating the aperture synthesis processing, and in reality, the aperture synthesis processing unit 44 generates the reception beam data Rb for about 8 to 48 scanning line positions for one transmission beam.

Next, the transmission/reception unit 40 transmits a transmission beam #2 of which the position is shifted with respect to the transmission beam #1 in the scanning direction, and receives a reception beam #2 for the transmission beam #2. In the example of FIG. 10, the transmission/reception unit 40 transmits the transmission beam #2 centered on the scanning line position j=6, thereby receiving the reception beam #2 corresponding to the scanning line positions j=2 to 10. In the reception beam #2, k=j−1. Thereafter, the transmission/reception unit 40 transmits a transmission beam #3 of which the position is further shifted with respect to the transmission beam #2 in the scanning direction, and receives a reception beam #3 for the transmission beam #3. In the example of FIG. 10, the transmission/reception unit 40 transmits the transmission beam #3 centered on the scanning line position j=7, thereby receiving the reception beam #3 corresponding to the scanning line positions j=3 to 11. In the reception beam #3, k=j−2.

By repeating such processing, the plurality of reception beam data Rb can be obtained for one scanning line position j. The maximum number of the reception beam data Rb obtained for one scanning line position j is the same as the number of times of the transmission of the transmission beam. In a case in which the transmission beam number (reception beam number) is represented by h and the reception beam data Rb corresponding to the in-beam position k in the reception beam #h is represented by LRI(h,k), in a case in which the number of the reception beam data Rb included in the reception beam #h is nine, for example, the reception beam data Rb corresponding to the scanning line position of j=12 is the following nine data.

LRI(4,9), LRI(5,8), LRI(6,7), LRI(7,6), LRI(8,5), LRI(9,4), LRI(10,3), LRI(11,2), LRI(12,1)

The aperture synthesis processing unit 44 adds (synthesizes) the plurality of reception beam data Rb corresponding to the same scanning line position j to generate the addition reception beam data corresponding to each scanning line position j. It should be noted that the aperture synthesis processing has an effect of improving the S/N ratio or the resolution in the azimuth direction.

In the present embodiment, the aperture synthesis processing unit 44 generates a plurality of addition reception beam data having different addition numbers of the plurality of reception beam data Rb corresponding to the same scanning line position j by the control from the controller 34. For example, the aperture synthesis processing unit 44 generates the plurality of addition reception beam data in which the addition numbers of the reception beam data Rb are 3, 5, 7, and 9. For example, in a case in which the addition reception beam data at the scanning line position of j=12 is described as $RF_{J=12}(N)$ (N is the addition number), as described above, in a case where nine reception beam data Rb corresponding to the scanning line position of j=12 are acquired, the addition reception beam data $RF_{J=12}(N)$ in a case in which the addition numbers are 3, 5, 7, and 9 are, for example, as follows.

$$RF_{J=12}(3)=LRI(7,6)+LRI(8,5)+LRI(9,4)$$

$$RF_{J=12}(5)=LRI(6,7)+LRI(7,6)+LRI(8,5)+LRI(9,4)+\\LRI(10,3)$$

$$RF_{J=12}(7)=LRI(5,8)+LRI(6,7)+LRI(7,6)+LRI(8,5)+\\LRI(9,4)+LRI(10,3)+LRI(11,2)$$

$$RF_{J=12}(9)=LRI(4,9)+LRI(5,8)+LRI(6,7)+LRI(7,6)+\\LRI(8,5)+LRI(9,4)+LRI(10,3)+LRI(11,2)+LRI\\(12,1)$$

Of course, the reception beam data Rb that is the addition target is not limited to the above, and for example, in a case in which the addition number is 3, LRI(6,7), LRI(8,5), and LRI(10,3) may be added.

In the present embodiment, the aperture synthesis processing unit 44 generates the plurality of addition reception beam data (addition frame data) for one frame having different addition numbers of the reception beam data Rb. It should be noted that the aperture synthesis processing unit 44 does not always have to generate the addition reception beam data for the entire one frame for one addition number, and need only generate the addition reception beam data that covers at least a target region for enhancing an image quality of the ultrasound image.

In the second embodiment, as described above, the aperture synthesis processing unit 44 corresponds to an addition data generation unit.

The plurality of addition reception beam data having different addition numbers of the reception beam data Rb generated by the aperture synthesis processing unit 44 are stored in a beam data memory 46. FIG. 4 shows a plurality of addition reception beam data SRb which have different addition numbers of the reception beam data Rb and are stored in the beam data memory 46. Similar to the first embodiment, in the second embodiment as well, the plurality of regions Re are defined in advance in the data space of the addition reception beam data SRb. It should be noted that, since the data space of the addition reception beam data SRb is a data space defined by the azimuth direction and the depth direction as in the data space of the reception beam data Rb, the data space of the addition reception beam data SRb and the data space of the reception beam data Rb are substantially synonymous.

The S/N estimation unit 48 executes frequency analysis with respect to each of the plurality of addition reception beam data SRb having different addition numbers of the reception beam data Rb before the detection processing (that is, having frequency information) for each region Re. As a result, the frequency spectrum (see FIG. 5) is acquired for each region Re and for each addition number of the reception beam data Rb.

Similar to the first embodiment, the S/N estimation unit 48 calculates spectral intensity Si for each frequency domain F based on the acquired frequency spectrum, and acquires the spectral intensity Si for each region Re, for each addition number of the reception beam data Rb, and for each frequency domain F. Then, the S/N estimation unit 48 plots the spectral intensity for the addition number of each reception beam data Rb for one region Re and one frequency domain F in the two-dimensional data space of the addition number of the reception beam data Rb and the spectral intensity (see FIG. 6). Then, the S/N estimation unit 48 obtains an approximate straight line AP of the plotted spectral intensity for the addition number of each of the reception beam data Rb, and calculates a slope of the approximate straight line AP.

Even in this case, the slope of the approximate straight line AP is a parameter indicating an S/N indicator of the region Re in the frequency domain F. Similar to the reception channel signal in the first embodiment, the signal components of the plurality of reception beam data Rb corresponding to the same scanning line position are signals having substantially the same phase and substantially the same amplitude. Therefore, ideally, in a case in which N signal components are added, the signal components in each frequency domain F are each multiplied by about N. On the other hand, the phases and the amplitudes of the noise components of the plurality of reception beam data Rb corresponding to the same scanning line position vary. Therefore, even in a case in which N noise components are added, the noise component in each frequency domain F is not multiplied by N and is only a value smaller than the value multiplied by N (approximately multiplied by $\sqrt{N}$).

Therefore, as the number of the signal components of the plurality of reception beam data Rb corresponding to the same scanning line position is increased, the S/N indicator is increased as the addition number is increased. In other words, the slope of the approximate straight line AP of the spectral intensity for the addition number of each reception beam data Rb represents the S/N indicator.

As described above, ideally, in a case in which N signal components of the plurality of reception beam data Rb corresponding to the same scanning line position are added, the signal component of each frequency domain F is multiplied by N. However, there may be a case in which such a situation does not occur. For example, the signal component of the reception beam data Rb (for example, the reception beam data Rb corresponding to the scanning line position 5 in the reception beam #1 in FIG. 10) corresponding to the scanning line position close to the center of the transmission beam may be larger than the signal component of the reception beam data Rb (for example, the reception beam data Rb corresponding to the scanning line position 1 in the reception beam #1 in FIG. 10) corresponding to the scanning line position far from the center of the transmission beam. Therefore, for example, in a case in which two reception beam data Rb (for example, LRI(8,5) and LRI(9,4)) close to the center of the transmission beam are added in a case in which the addition number is 2, and the reception beam data Rb (for example, LRI(5,8), LRI(8,5), LRI(9,4), and LRI(12, 1)) including the reception beam data Rb far from the center of the transmission beam are added in a case in which the addition number is 4, even in a case in which all the reception beam data Rb are the signal components, the spectral intensity in a case in which the addition number is 4 may not be doubled as compared with a case in which the addition number is 2.

Therefore, the S/N estimation unit 48 may correct the spectral intensity for each addition number based on a correction coefficient defined in advance for each addition number of the reception beam data Rb. The correction coefficient need only be defined in advance based on the in-beam position k of the reception beam data Rb that is the addition target in each addition number of the reception beam data Rb or the like, and need only be stored in the memory 32. Then, the S/N estimation unit 48 may calculate the corrected spectral intensity obtained by correcting the spectral intensity for each addition number based on the correction coefficient for each addition number, obtain the approximate straight line AP of the corrected spectral intensity for each addition number (see FIG. 7), and estimate the slope of the approximate straight line AP as the S/N indicator.

The S/N estimation unit 48 performs the processing described above for each combination of the region Re and the frequency domain F, and calculates the slope of the approximate straight line AP for each combination of the region Re and the frequency domain F. That is, the S/N estimation unit 48 estimates the S/N indicator for each combination of the region Re and the frequency domain F based on the increase amount of the spectral intensity accompanying the increase of the addition number of the reception beam data Rb (see FIG. 8).

The signal processing unit 42 generates, for each region Re, the bandpass filter that passes signals in the frequency domain F in which the estimated S/N indicator is equal to or larger than a predetermined S/N threshold value. For example, for the region Re having the S/N indicator for each frequency domain F shown in FIG. 8, the bandpass filter that passes signals from a frequency f1 to a frequency f2 is generated. Since the S/N indicators for each frequency domain F may be different from each other between the respective regions Re, the bandpass filters generated for the respective regions Re may also be different from each other.

The signal processing unit 42 applies the bandpass filter generated for each region Re to the reception beam data Rb before the detection processing as the image quality enhancement processing of enhancing the image quality of the ultrasound image. In other words, even in a case in which the S/N indicator for each frequency domain F is different for each region Re, the bandpass filter suitable for each region Re can be applied. As a result, it is possible to adaptively enhance the image quality of each region Re of the ultrasound image. For example, in the ultrasound image, appropriate noise reduction can be executed without excessively performing noise suppression for each position (region Re) and impairing resolution. As described above, in the second embodiment as well, the signal processing unit 42 corresponds to an image quality enhancement unit.

The signal processing unit 42 can apply the bandpass filter described above to the reception beam data Rb in the same frame as the reception beam data Rb that is the source of the plurality of addition reception beam data SRb stored in the beam data memory 46. In addition, from the viewpoint of suppressing delay due to the generation processing of the plurality of addition reception beam data SRb having different addition numbers of the reception beam data Rb, the estimation processing of the S/N indicator by the S/N estimation unit 48, and the like, the signal processing unit 42 may set the reception beam data Rb that is the application target of the bandpass filter as the reception beam data Rb of one frame after the reception beam data Rb, which is a source of the plurality of addition reception beam data SRb. Further, in a case in which there is no change in the cross section of the subject shown in the ultrasound image, it is considered that the S/N indicator of each frequency domain F in each region Re is not changed so much. Therefore, in the second embodiment as well, the signal processing unit 42 may continue to use the bandpass filter of each region Re once generated until the cross section of the subject shown in the ultrasound image is changed.

Third Embodiment

FIG. 11 is a schematic configuration diagram of an ultrasound diagnostic apparatus 10-3 according to a third embodiment. In FIG. 11, components that execute the same processing as the processing of the ultrasound diagnostic apparatus 10 according to the first embodiment are designated by the same reference numerals as the reference numerals in FIG. 1, and the description thereof will be omitted.

A transmission/reception unit 50 as a reception beam data generation unit transmits the transmission signal to the ultrasound probe 12 under the control of the controller 34. As a result, the ultrasound waves are transmitted from each oscillation element toward the subject. The ultrasound waves are transmitted from the plurality of oscillation elements at a time, and the ultrasound beams are transmitted to the transmission/reception unit 50 in the plurality of directions from the plurality of oscillation elements by controlling the transmission timing of the ultrasound waves from each oscillation element. In addition, the transmission/reception unit 50 receives a reception channel signal from each oscillation element that receives the reflected waves from the subject. The transmission/reception unit 50 executes the phase adjustment addition processing with respect to the plurality of reception channel signals corresponding to the plurality of reception channels, to generate the reception beam data Rb.

The signal processing unit 52 executes various types of signal processing including, for example, the filter processing of applying the bandpass filter to the reception beam data Rb from the transmission/reception unit 50. In particular, the signal processing unit 52 generates the bandpass filter for each region Re based on the S/N indicator, for each region Re and for each frequency domain F, which is estimated by an S/N estimation unit 58 described later. Details of generation processing of the bandpass filter will be described later.

In addition, the signal processing unit 52 may not perform the bandpass filter processing with respect to the reception beam data Rb constituting the frame data used by the S/N estimation unit 58 described later. Alternatively, as the preprocessing, the bandpass filter processing having a wide band characteristic that cuts only a component in the vicinity of DC may be performed.

The reception beam data Rb subjected to the signal processing by the signal processing unit 52 is held in a memory (not shown) called an LRI memory. The LRI memory has at least a memory capacity capable of storing the reception beam data Rb for the plurality of frames.

A frame addition unit 54 generates the addition reception beam data for one frame by adding the frame data which are the plurality of reception beam data Rb for one frame. Specifically, the frame addition unit 54 adds the plurality of frame data such that the reception beam data Rb corresponding to the same scanning line position is added, to generate the addition reception beam data for one frame. In addition, the frame addition unit 54 generates the plurality of addition reception beam data (hereinafter, referred to as "addition frame data") for one frame having different addition numbers of the frame data.

The plurality of frame data to be added by the frame addition unit 54 are the frame data obtained based on the transmission beams transmitted to the same scanning surface. That is, each frame data includes the reception beam data Rb corresponding to the same scanning line position. For example, the plurality of frame data to be added by the frame addition unit 54 are the frame data continuously acquired in time series while the posture of the ultrasound probe 12 is maintained.

In the third embodiment, as described above, the frame addition unit 54 corresponds to an addition data generation unit.

The plurality of addition frame data, which have different addition numbers of the frame data and are generated by the frame addition unit 54, are stored in a frame data memory 56. Similar to the first embodiment, in the third embodiment, the plurality of regions Re are defined in advance in the data space of the frame data (that is, the reception beam data Rb).

The S/N estimation unit 58 executes frequency analysis with respect to each of the reception beam data Rb before the detection processing (that is, having frequency information) constituting the plurality of addition frame data having different addition numbers of the frame data for each region Re. As a result, the frequency spectrum (see FIG. 5) is acquired for each region Re and for each addition number of the frame data.

Similar to the first embodiment, the S/N estimation unit 58 calculates spectral intensity Si for each frequency domain F based on the acquired frequency spectrum, and acquires the spectral intensity Si for each region Re, for each addition number of the frame data, and for each frequency domain F. Then, the S/N estimation unit 58 plots the spectral intensity for the addition number of each frame data for one region Re and one frequency domain F in the two-dimensional data space of the addition number of the frame data and the spectral intensity (see FIG. 6). Then, the S/N estimation unit 58 obtains an approximate straight line AP of the plotted spectral intensity for the addition number of each of the frame data, and calculates a slope of the approximate straight line AP.

Even in this case, the slope of the approximate straight line AP is a parameter indicating an S/N indicator of the region Re in the frequency domain F. Similar to the reception channel signal in the first embodiment, the signal components of the plurality of reception beam data Rb corresponding to the same scanning line position are signals having substantially the same phase and substantially the same amplitude. Therefore, ideally, in a case in which N signal components are added, the signal components in each frequency domain F are each multiplied by about N. On the other hand, the phases and the amplitudes of the noise components of the plurality of reception beam data Rb corresponding to the same scanning line position vary. Therefore, even in a case in which N noise components are added, the noise component in each frequency domain F is not multiplied by N and is only a value smaller than the value multiplied by N (approximately multiplied by $\sqrt{N}$).

Therefore, as the number of the signal components of the plurality of reception beam data Rb corresponding to the same scanning line position is increased, the S/N indicator is increased as the addition number is increased. In other words, the slope of the approximate straight line AP of the spectral intensity for the addition number of each frame data represents the S/N indicator.

The S/N estimation unit 58 performs the processing described above for each combination of the region Re and the frequency domain F, and calculates the slope of the approximate straight line AP for each combination of the region Re and the frequency domain F. That is, the S/N estimation unit 58 estimates the S/N indicator for each combination of the region Re and the frequency domain F based on the increase amount of the spectral intensity accompanying the increase of the addition number of the frame data (see FIG. 8).

The signal processing unit 52 generates, for each region Re, the bandpass filter that passes signals in the frequency domain F in which the estimated S/N indicator is equal to or larger than a predetermined S/N threshold value. For example, for the region Re having the S/N indicator for each frequency domain F shown in FIG. 8, the bandpass filter that passes signals from a frequency f1 to a frequency f2 is generated. Since the S/N indicators for each frequency domain F may be different from each other between the respective regions Re, the bandpass filters generated for the respective regions Re may also be different from each other.

The signal processing unit 52 applies the bandpass filter generated for each region Re to the reception beam data Rb before the detection processing as the image quality enhancement processing of enhancing the image quality of the ultrasound image. In other words, even in a case in which the S/N indicator for each frequency domain F is different for each region Re, the bandpass filter suitable for each region Re can be applied. As a result, it is possible to adaptively enhance the image quality of each region Re of the ultrasound image. For example, in the ultrasound image, appropriate noise reduction can be executed without excessively performing noise suppression for each position (region Re) and impairing resolution. As described above, in the third embodiment as well, the signal processing unit 52 corresponds to an image quality enhancement unit.

The signal processing unit 52 can apply the bandpass filter described above to the reception beam data Rb of the next frame of the reception beam data Rb constituting the plurality of frame data stored in the frame data memory 56. In addition, in a case in which there is no change in the cross section of the subject shown in the ultrasound image, it is considered that the S/N indicator of each frequency domain F in each region Re is not changed so much. Therefore, in the third embodiment as well, the signal processing unit 52 may continue to use the bandpass filter of each region Re once generated until the cross section of the subject shown in the ultrasound image is changed.

Although the embodiments according to the present invention have been described above, the present invention is not limited to the embodiments described above, and various modifications can be made without departing from the gist of the present invention.

What is claimed is:

1. An ultrasound diagnostic apparatus comprising:
   a controller configured to:
   generate reception beam data by adding a plurality of reception channel signals, which are obtained by transmitting and receiving ultrasound waves to and from a subject and correspond to a plurality of reception channels and of which phases are adjusted by phase adjustment processing, the controller generating a plurality of the reception beam data having different quantities of the reception channel signals;
   execute frequency analysis with respect to each of the plurality of reception beam data before detection processing having different quantities of the reception channel signals for each predetermined region in a data space of the reception beam data, to estimate an S/N indicator based on an increase amount of spectral intensity accompanying an increase of the quantity for each region and for each frequency domain; and execute different types of image quality enhancement processing for each region to enhance an image quality of an ultrasound image based on the S/N indicator estimated for each region and for each frequency domain.

2. The ultrasound diagnostic apparatus according to claim 1, wherein the controller generates a bandpass filter for each region based on the S/N indicator estimated for each region and for each frequency domain, to apply the generated bandpass filter for each region to the reception beam data before the detection processing.

3. The ultrasound diagnostic apparatus according to claim 1, wherein the controller calculates a slope of an approximate straight line of the spectral intensity for each quantity in a two-dimensional data space of the quantity and the spectral intensity for each region and for each frequency domain, to estimate the calculated slope as the S/N indicator for each region and for each frequency domain.

4. The ultrasound diagnostic apparatus according to claim 3, wherein the controller calculates corrected spectral intensity obtained by correcting the spectral intensity based on a predetermined correction coefficient for each quantity, to estimate the slope of the approximate straight line of the corrected spectral intensity for each quantity in the two-dimensional data space as the S/N indicator.

* * * * *